(12) United States Patent
Alfaro et al.

(10) Patent No.: US 9,603,552 B2
(45) Date of Patent: Mar. 28, 2017

(54) MEASURING METHOD, PEDESTAL AND MEASURING SYSTEM FOR DETERMINING BIOMETRIC DATA OF HUMAN FEET

(71) Applicant: VITRONIC Dr.-Ing. Stein Bildverarbeitungssysteme GmbH, Wiesbaden (DE)

(72) Inventors: Alejandro Arrieta Alfaro, Mannheim (DE); Burghard Hoffmann, Taunusstein (DE); Udo Bürgel, Wiesbaden (DE); Ales Jurca, Spodnja Idrija (SI)

(73) Assignee: VITRONIC Dr.-Ing. Stein Bildverarbeitungssysteme GmbH, Wiesbaden (DE)

( * ) Notice: Subject to any disclaimer, the term of this patent is extended or adjusted under 35 U.S.C. 154(b) by 83 days.

(21) Appl. No.: 14/736,616

(22) Filed: Jun. 11, 2015

(65) Prior Publication Data

US 2015/0359461 A1    Dec. 17, 2015

(30) Foreign Application Priority Data

Jun. 11, 2014    (EP) .................................... 14172025

(51) Int. Cl.
  *A61B 5/107*   (2006.01)
  *A43D 1/02*    (2006.01)
  *A61B 5/00*    (2006.01)

(52) U.S. Cl.
  CPC ............ *A61B 5/1074* (2013.01); *A43D 1/025* (2013.01); *A61B 5/0079* (2013.01);
  (Continued)

(58) Field of Classification Search
  CPC .............................. A61B 5/1074; A43D 1/025
  (Continued)

(56) References Cited

U.S. PATENT DOCUMENTS 5,025,476 A * 6/1991 Gould ................. A61B 5/1074
                                                    33/3 B
5,164,793 A * 11/1992 Wolfersberger ....... A43D 1/025
                                                    33/3 R
(Continued)

FOREIGN PATENT DOCUMENTS

AU      2004202110        12/2004
DE      102011007678 A1   10/2012
(Continued)

*Primary Examiner* — Christopher Fulton
(74) *Attorney, Agent, or Firm* — Dinsmore & Shohl LLP

(57) ABSTRACT

The invention relates to a measuring method for determining biometric data of human feet, comprising the following steps providing a reference object, which has at least one reference pattern, providing a freely moveable image recording device, automatically detecting the relative position and the alignment of the image recording device relative to the reference object using the at least one reference pattern, automatically recording of several images by the image recording device, wherein each individual image is only recorded, when the relative position and the alignment of the image recording device relative to the reference object corresponds to a triggering position predetermined for the respective image, determining biometric data of the at least one foot by means of the recorded images.

Furthermore, the present invention relates to a measuring system as well as a pedestal for determining biometric data of human feet.

16 Claims, 2 Drawing Sheets

(52) U.S. Cl.
CPC ............ *A61B 5/1079* (2013.01); *A61B 5/706* (2013.01); *A61B 5/742* (2013.01); *A61B 5/7405* (2013.01); *A61B 2503/12* (2013.01); *A61B 2576/02* (2013.01)

(58) Field of Classification Search
USPC ...................................... 33/515, 3 R; 382/115
See application file for complete search history.

(56) References Cited

U.S. PATENT DOCUMENTS

| | | | | |
|---|---|---|---|---|
| 5,689,446 | A * | 11/1997 | Sundman | A43D 1/02 33/3 A |
| 5,753,931 | A * | 5/1998 | Borchers | A43D 1/025 250/559.05 |
| 5,911,126 | A * | 6/1999 | Massen | A43D 1/025 348/E13.015 |
| 6,289,107 | B1 * | 9/2001 | Borchers | A43D 1/02 356/391 |
| 6,546,356 | B1 | 4/2003 | Genest | |
| 6,549,639 | B1 | 4/2003 | Genest | |
| 6,909,513 | B1 * | 6/2005 | Fujita | G01B 11/245 12/142 R |
| 7,433,502 | B2 * | 10/2008 | Rutschmann | A61B 5/0064 382/128 |
| 9,019,359 | B2 * | 4/2015 | Leedy | A43D 1/025 348/77 |
| 2009/0051683 | A1 * | 2/2009 | Goonetilleke | A43D 1/025 345/419 |
| 2014/0118538 | A1 * | 5/2014 | Hoffmann | H04N 5/2256 348/136 |

FOREIGN PATENT DOCUMENTS

| | | | |
|---|---|---|---|
| DE | 102011116727 A1 | 4/2013 | |
| DE | 102011121086 A1 | 6/2013 | |
| DE | EP 2954798 A1 * | 12/2015 | ............ A43D 1/025 |
| EP | 2641539 A1 | 9/2013 | |
| HU | EP 2949270 A1 * | 12/2015 | ............ A43D 1/025 |
| JP | WO 2004075677 A1 * | 9/2004 | ............ A43D 1/025 |
| WO | 2013071416 A1 | 5/2013 | |

* cited by examiner

MEASURING METHOD, PEDESTAL AND MEASURING SYSTEM FOR DETERMINING BIOMETRIC DATA OF HUMAN FEET

CROSS-REFERENCE TO RELATED APPLICATIONS

This application claims priority of European Patent Application 14172025.0-1658 filed Jun. 11, 2014, the contents of which are incorporated herein by reference.

FIELD OF THE INVENTION

The present invention relates to a measuring method as well as a measuring system for determining biometric data of human feet. Furthermore, the present invention relates to a pedestal for determining biometric data of human feet, comprising a base plate, on which at least one human foot, which is to be measured, can be placed, wherein the base plate has a geometric base-sided reference pattern.

BACKGROUND OF THE INVENTION

Biometric data is generally such data, which can be determined during the body measuring of human beings. By the example of the human foot, the biometric data can comprise the length of the foot, the foot width and the foot height as well as a three-dimensional representation of the foot.

A measuring system for determining the length and the width of a human foot is for example known from DE 10 2011 116 727 A1. This measuring system has an illuminated base plate with a geometric base-sided reference pattern. Furthermore, a freely movable camera is provided to record a foot placed on the base plate.

It is seen to be disadvantageous that the known measuring system is only suitable to determine the length and the width of a human foot.

From DE 10 2011 007 678 A1 a measuring system is known on which base plate marking lines are attached for the longitudinal alignment of the foot to be measured. An abutment projects at an end of the base plate, against which the heel of the foot is to be put. At the opposite end of the base plate, an image recording device is held rigidly, which records from diagonally above images of the foot to be measured. To achieve two views of the foot with one image recording, a mirror system is provided in the viewing field of the image recording device.

A further similar measuring system is known from AU 2004 0 202 110 A1. The known measuring system has a base plate provided with centimeter markings and on which the foot to be measured is aligned. On the base plate, mirrors project laterally. On the base plate, an imaging recording device is mounted, which is aligned rigidly towards the base plate and the mirrors.

It is disadvantageous in these prior embodiments that the foot to be measured has to be aligned initially. Furthermore, the measuring system is, because of the image recording device mounted rigidly on the base plate and because of the mirror system, large in size and cumbersome in operating.

SUMMARY OF THE INVENTION

Thus, the object of the present invention is, to provide a pedestal for determining biometric data of human feet, with which besides the length and the width further biometric data of the feet can be determined in a simple manner.

This object is met according to the invention by a pedestal of the above named type wherein the pedestal includes a wall element which splits the base plate into two halves and which is arranged transversally to the base plate, for each half of the base plate a mirror arranged transversally to the base plate, wherein the wall element has on the sides facing the mirrors respectively a geometric wall-sided reference pattern and wherein respectively a reflective mirror face of the mirrors is arranged opposite to one of the wall-sided reference patterns.

According to the invention, it is provided that by means of the wall-sided reference pattern, aligned transversally to the base-sided reference pattern, a spatial reference system is formed, in which at least one human foot to be measured can be placed. Thus, not only two-dimensional, rather also three-dimensional biometric data of the at least one foot can be determined in a simple manner. By the three-dimensional reference pattern system, a traceable reference system is provided, so that the at least one foot to be measured can be placed on the pedestal in a simple manner, without the requirement that the heel of the foot has to be put against an abutment. Furthermore, the pedestal according to the invention is especially suitable for computer aided image analysis methods for calculating three-dimensional models of the at least one foot. The reference pattern can for example be formed as point markers or calibration markings or as regular line patterns. Besides human feet, the biometric data of any other body part of a human being, for example the human hand or of an animal body part, can also be determined. In this case, all biometric data of body parts of creatures can be determined, which can be represented two- or three-dimensionally and can be placed on the pedestal according to the invention.

In a preferred manner, the wall element and the base element are arranged at an angle to each other, which is in the range between 70 and 140 degrees. In this case, it is the angle, which encompasses the upper side of the base plate, facing the foot, and the outer side of the wall element facing the foot. To be able to determine in a simple manner and exactly the height of the foot, the wall element is preferably arranged at a right angle to the base plate. In a preferred embodiment, the wall element is directly attached to the base plate.

According to an aspect of the present invention, the base plate and/or the wall element can have a retro-reflective surface, i.e. the incident radiation is as far as possibly reflected independently of the alignment of the retro-reflective surface at least to a large part in direction back to the radiation source. This is especially suitable for such cases, in which the at least one foot to be measured is recorded, to determine the biometric data by means of image analysis methods on a computer. Because of the retro-reflective surface, the at least one foot to be measured is represented as a dark area on the images, when using a flash rich in contrast. Thus, the image contrast of the image recording is increased, so that during the image analysis method the at least one to be measured human foot can be separated from the pedestal in a better manner. In the simplest manner, the retro-reflective surface is provided by a foil, which is glued to the surface of the base plate. The geometric base-sided and/or the wall-sided reference pattern(s) can be attached for example on the foil or in the case of a transparent foil directly on the base plate. Furthermore, the retro-reflective surface of the base plate and/or of the wall element can be for example an upper layer of the base plate or of the wall element.

In preferred manner, the mirrors each are arranged to the base plate at an angle which is in the range between 70 and 160 degrees. Thus, during the image recording with a camera, several views of the at least one foot can be recorded in one image at the same time. For example, besides the top view of the at least one foot, the mirror side view of the at least one foot can be recorded.

To be able to place two feet on the pedestal in a simple manner at the same time and to be able to determine their biometric data, the pedestal can be formed symmetrically to a plane formed by the wall element. Thus, the wall element splits the pedestal into two symmetrical halves so that the base plate has on both surfaces contacting the to be measured feet a base-sided reference pattern and the wall element has on both outer sides facing the feet a wall-sided reference pattern.

A further subject of the present invention is a measuring system for determining biometric data of human feet, which besides the above described pedestal comprises according to the invention a freely movable image recording device for recording several images of the at least one placed foot. The image recording device formed as a portable hand-held device, can for example be a tablet-PC or a smart phone.

Advantageously, it is provided that the measuring system comprises a processing device, which is formed such, that a three-dimensional model of the at least one foot can be generated from the images and that biometric data of the at least one foot can be determined by using the model. In this case, the model can be a rudimentary three-dimensional model of the foot to be measured based on a point cloud. The model can also comprise a two-dimensional top view onto the foot and a two-dimensional side view of the foot, which are combined to a simplified three-dimensional model. It is also conceivable that the model comprises a three-dimensional representation of the surface of the foot to be measured.

Furthermore, the measuring system can have an evaluation device formed such, that the determined biometric data is comparable with sets of data of shoes using stored shoe sizes and/or shoe shapes and that the shoes fitting to the determined biometric data are identifiable.

Furthermore, the measuring system can comprise an out-put device, formed such, that information concerning the fitting shoes are reproducible.

In a preferred embodiment the image recording device and the out-put device form a portable structural unit and that the processing device as well as the evaluation device are structurally separated from the image recording device and the out-put device. Preferably, the processing device and the evaluation device are formed by a processing unit, which are provided in a central server, which communicates via an internet line with the image recording device. The images recorded by the image recording device can be transferred via an internet connection to the processing device, which calculates a model of the at least one foot using the images. Furthermore, the evaluation device can identify by means of the at least one determined three-dimensional model of the at least one foot fitting shoes using the stored three-dimensional shoe models or especially by using the calculated foot length, foot width and/or foot height. The identified shoes can be transmitted then combined in a hit list to the out-put device, to present the fitting shoes to the customer. Besides the above described structural combination of the image recording device and the out-put device to a unit, other combinations are possible. Also the image recording device, the processing device, the evaluation device and the out-put device can be individual devices structurally separated from each other or can be integrated together in a multifunctional device, especially a portable hand-held device.

A further subject of the present invention relates to a measuring method for determining biometric data of human feet, which comprises according to the invention the following steps: providing a reference object, which has at least one reference pattern, providing a freely moveable image recording device, automatically detecting the relative position and the alignment of the image recording device relative to the reference object using the at least one reference pattern, automatically recording several images by the image recording device, wherein each individual image is only recorded, when the relative position and the alignment of the image recording device relative to the reference object corresponds to a triggering position predetermined for the respective image, determining biometric data of the at least one foot by means of the recorded images.

When the image recording device is aligned at least roughly on the reference object, this determines by means of the at least one reference pattern its relative position and its alignment to the reference object. In other words, the image recording device detects by means of the at least one reference pattern especially its distance, its height and its viewing angle to the reference object. Therefore, the image recording device can determine itself its position and its alignment in relation to the reference object and can automatically record the images, when especially a user holds it in the predetermined triggering positions. Commonly for generating a three-dimensional model at least two images of different views are necessary for each foot, so that for each foot to be measured at least two triggering points can be predetermined. For example a first triggering point can be defined by a position in front of the reference object, i.e. in extension of the at least one foot and a further position can be defined laterally from the reference object with respectively predetermined distances to the reference object.

In a preferred manner the step of determining the biometric data of the at least one foot by means of the recorded images comprises at least the following partial steps: generating at least one three-dimensional model of the at least one foot placed on the reference object by a processing device on the basis of the recorded images and determining the biometric data of the at least one foot by the processing device using the at least one three-dimensional model.

Advantageously, the above described pedestal is used as the reference object in the frame of the method. The pedestal according to the invention is especially suitable for computer aided image analysis methods for calculating three-dimensional models of the at least one foot.

Furthermore, the above described measuring system can be used for carrying out the measuring method. For this, the at least one to be measured human foot is placed on the base-sided reference pattern of the pedestal. The freely movable image recording device determines automatically its relative position and its alignment to the pedestal by means of the at least one base-sided reference pattern and/or by means of the at least one wall-sided reference pattern. In this case, the image recording device records automatically an image, when its relative position and alignment to the pedestal correspond to a triggering position predetermined for the respective image.

According to an aspect of the measuring method according to the invention the following step is furthermore provided: putting of instructions for guiding a image recording device to the respective triggering position. So the user of the freely movable image recording device knows, where the predetermined triggering points are, this outputs instructions, to guide the user to an active guiding of the image recording device into one of the triggering positions. The image recording device can additionally or alternatively output a list of all triggering points in relation to the reference object and especially to its present position, so that the user can quickly find the individual triggering positions.

Advantageously, before the out-put of the respective instruction for guiding the image recording device to the respective triggering position, the following steps are carried out: automatically detecting the relative position and the alignment of the image recording device to the reference object by using the at least one reference pattern, calculating a path from the determined relative position with the determined alignment to the respective triggering position. The instructions can comprise commands like move the image recording device closer or further away from the reference object, pivot to the left or right, pivot upwards or downwards, move in clockwise direction or anti-clockwise direction to the reference object, hold higher or lower.

Advantageously, the instructions for guiding the user can be carried out via optical or acoustical indication elements. For example, the image recording device or the out-put device can have a display and/or a loud speaker, via which the instructions are output. In preferred manner in an optical representation, simple image symbols, like for example arrows, are used, to prompt the user to an active guiding of the camera to the respective triggering points.

Furthermore, according to a further aspect of the measuring method according to the invention at least one of the following steps is provided: comparing the determined biometric data of the at least one foot with sets of data of shoes, which comprise at least information of shoe sizes or of shoe shapes of various shoes, by means of an evaluation device; transferring a hit list with the shoes fitting the biometric data from the evaluation device to the out-put device, and reproducing the information concerning the shoes listed in the hit list.

BRIEF DESCRIPTION OF THE DRAWINGS

A preferred embodiment of the invention is represented in the drawings and is described in the following. Herein it shows.

DETAILED DESCRIPTION OF THE PREFERRED EMBODIMENTS

Figure 1:
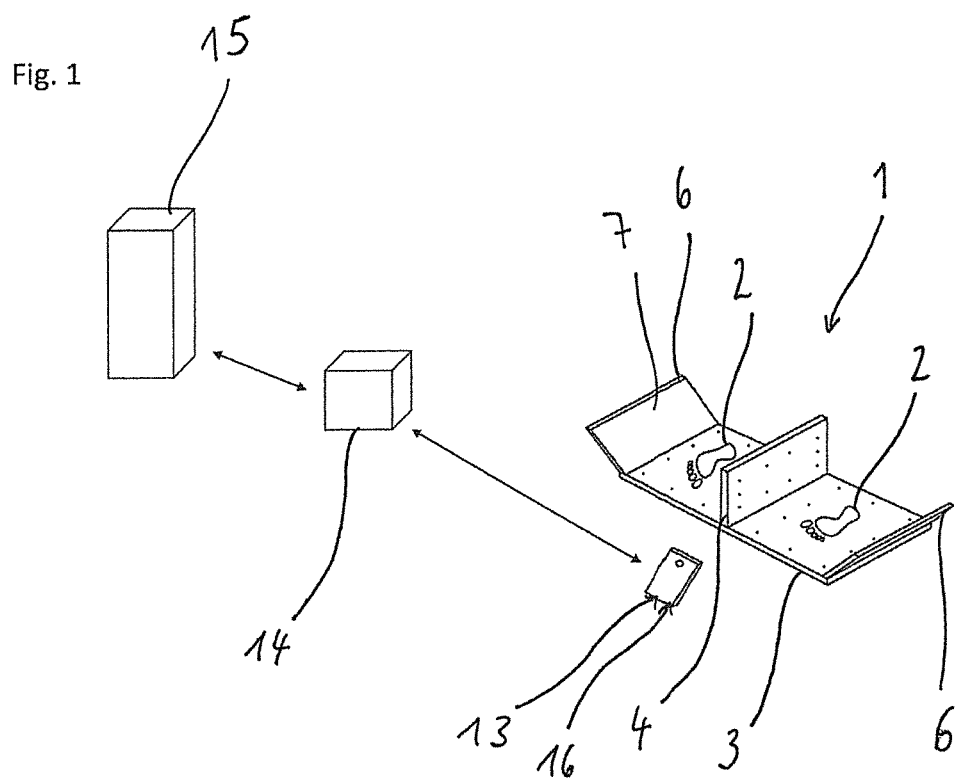
FIG. 1 a measuring system according to an embodiment in a schematical perspective view.

In the drawings an inventive measuring according to an embodiment of the present invention is shown. The measuring system serves for establishing three-dimensional models for determining biometric data of human feet. With the help of the measuring system for example shoe salespersons or online-platforms can propose to the customer shoes, fitting for his/her individual foot shape.

To the measuring system belongs a pedestal 1 according to the invention, onto which a person can step with both feet 2, which are here shown simplified as two foot prints. Precisely, the pedestal 1 has a rectangular base plate 3, onto which the two feet 2 can be placed at the same time. So that the person can take up a secure stand, the base plate 3 is aligned horizontally. Furthermore, a rectangular wall element 4 is provided, which is arranged at a right angle to the base plate 3 and is fixed thereto. The wall element 4 is aligned transversally to the longitudinal extension of the base plate 3 and forms a plane E, to which the whole pedestal 1 is formed symmetrically. In other words, the wall element 4 splits the base plate 3 into two halves, formed symmetrically to each other and on which left or right of the wall element 4 respectively one of the two feet 2 can be placed. At both outer longitudinal ends 5 of the base plate 3, respectively a mirror 6 is held on the base plate 3, which is arranged parallel to the wall element 4 and is arranged opposite thereto with its reflecting mirror face 7. The mirrors 6 are tilted by approximately 30 degrees from the vertical to the outside, so that the respective mirror 6 and the base plate 3 are arranged at an angle of approximately 120° to each other.

On the surfaces 8 of the base plate 3 coming into contact with the to be measured feet 2, and on the outer sides 11 of the wall element 4 facing to the feet 2, respectively, a retro-reflecting coating 9 is provided.

To be able to determine the biometric data of the feet 2, the retro-reflecting coating 9 has on both halves of the base plate 3, respectively a geometric base-sided reference pattern 10. Furthermore, the wall element 4 has on the two outer sides 11, facing to the mirrors 7, respectively a geometric wall-sided reference pattern 12. Each of the reference patterns 10, 12 is here formed of a multitude of reference points, which are arranged on a circumferential line of an imaginary rectangular.

Furthermore, the measuring system has a freely moveable, hand-held image recording device 13, by which several digital images of the feet 2, placed on the pedestal 1, can be taken. The image recording device 13, can for example be a commercial tablet-PC or a smart phone, which preferably is provided with a flash light. Because of the retro-reflecting surface 9 of the base plate 3 and of the wall element 4, the outlines of the feet 2 are distinctly visible during the image recording with flash light.

For calculating the three-dimensional models of the two feet 2, several views of each of the feet 2 placed on the pedestal 1 are necessary. Because of the mirror 6, the number of the necessary number can however be reduced, as with one image recording several views of at least one foot 2 can be taken at the same time. For example, besides the top view shown in FIG. 2 diagonally from the front onto the left foot 2, at the same time the mirror side view of the left foot 2 is recordable.

Figure 2:
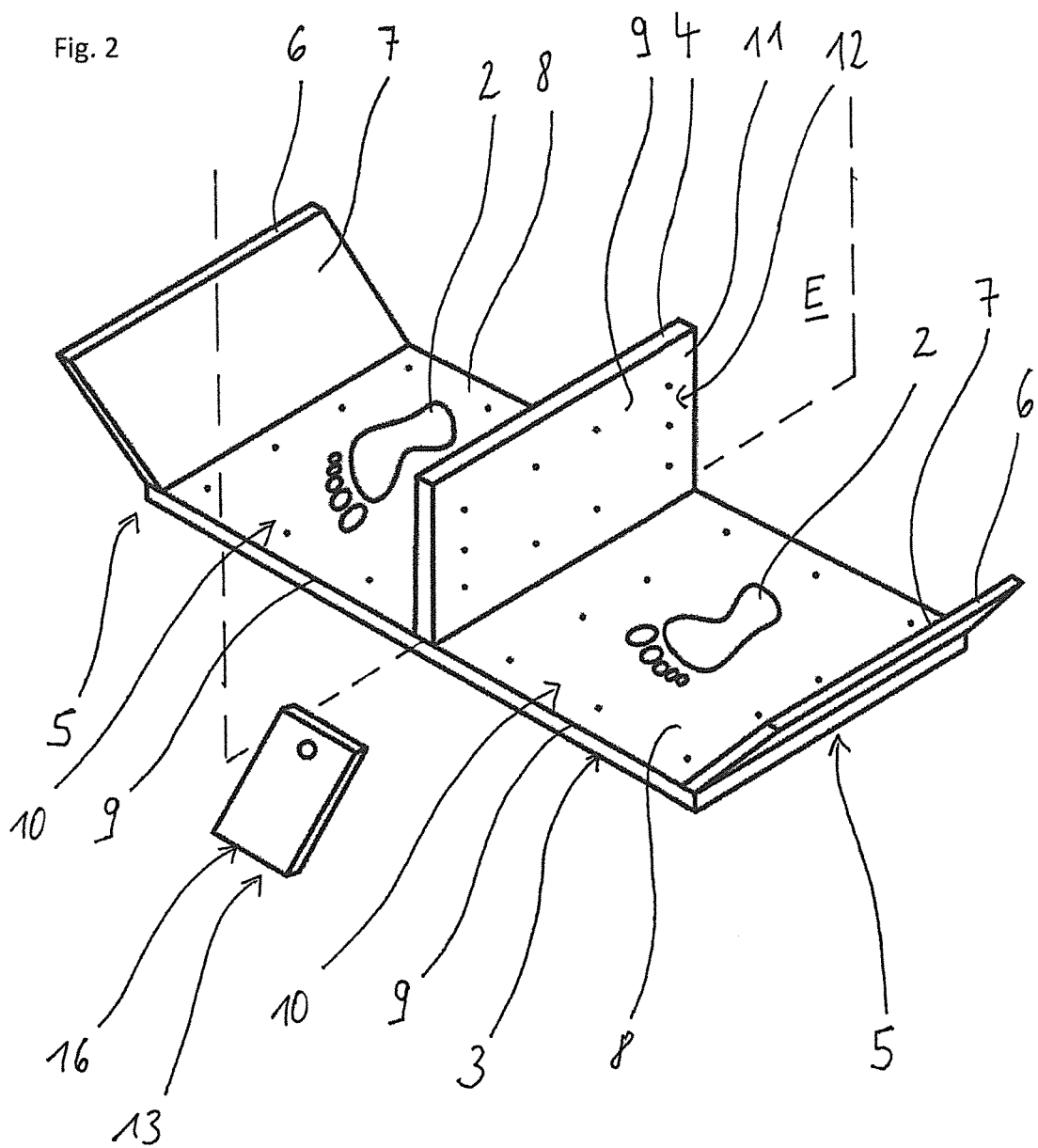
FIG. 2 a partial detail of the measuring system of FIG. 1 in a schematical perspective view.

With the image recording device 13, initially images of the first foot 2 and then of the second foot 2 are recorded from respectively several pre-determined triggering positions, especially from at least two triggering positions per foot 2. The different triggering positions are defined by means of the relative position and of the alignment of the image recording device 13 relative to the pedestal 1 for the left and for the right foot 2, whereby a reprojection in a three-dimensional world coordinate system is possible. In FIG. 2 one of the two triggering positions for the left foot 2 is shown exemplarily.

So that a user, for example the shoe salesperson, knows, where the predetermined triggering positions for the recording of the left or right foot 2 are, the image recording device 13 has a software for the automatic detection of its relative position and its alignment to the pedestal 1 by using the reference patterns 10, 12. If the image recording device 13 is arranged in one of the predetermined triggering positions for one of the images, it is automatically actuated. If however the image recording device 13 is not arranged in one of the triggering positions, it outputs instructions to the user, to request the user to an active transfer of the image recording device 13 into one of the triggering positions. For this, the image recording device 13 has a not shown display, which can graphically display instructions. For example, the user can be prompted by arrows to move the image recording device 13 to the right or left, to further tilt forwards or backwards, to move closer to or further away from the pedestal 1 or to hold the image recording device 13 higher or lower. Additionally or alternatively, the image recording device 13 can have a loudspeaker, by which instructions can be acoustically reproduced. As soon as the image recording device 13 detects that its relative position and its alignment to the pedestal 1 correspond to one of the triggering positions of a first image or to one of the following images, it automatically records the corresponding foot 2 with the view determined by the predetermined triggering position.

In advantageous manner, the image recording device 13 guides the user to the individual triggering positions in the following sequence: right foot from the front, left foot from the front, left foot from the back, right foot from the back.

After both feet 2 to be measured were recorded from all triggering positions necessary for the three-dimensional model, the digital image data is wirelessly transferred from the image recording device 13 to a processing device 14 of the measuring system in coded form. The image data has meta data in the known manner, which comprises here also information of the respective triggering position. The image data can also be transferred individually for the process optimisation after each image recording. The image recording device 13 and the processing device 14 are connected in this case to the same local network, wherein the processing device 14 can be a commercial PC, which for example is installed in a shop of the specialist shoe shop and can communicate with a multitude of image recording devices 13. The processing device 14 can however also be a central server, which can be connected to several image recording devices 13 at different places. Alternatively, the processing device can especially be integrated with the image recording device 13 in the hand-held tablet-PC or the smart phone.

The processing device 14 calculates the three-dimensional models of the two feet 2 by using the earlier recorded images, on which the outline of the feet and the reference patterns 10, 12, which are partially covered by the respective foot 2, are visible. From the image data of the different views of the feet 2, a three-dimensional model is reprojected in the world coordinate system by using the predetermined triggering positions. From the image data, point clouds are calculated in the world coordinate system, wherefrom furthermore inter alia the dimensions of the feet 2 in height, width and depth result.

The biometric data of the feet 2 and the generated three-dimensional feet models are transferred from the processing device 14 to an evaluation device 15 of the measuring system. The evaluation device 15 is in this case a central server connected to an internet connection, on which a multitude of sets of data of shoes is stored, which comprises for example shoe sizes and three-dimensional shoe models. The evaluation device 15 compares the determined biometric data of the measured feet 2 with the stored sets of data and transfers a hit list with shoes fitting to the biometric data via the processing device 14 to an out-put device 16. The out-put device 16 is combined with the image recording device 13 in a structural unit, which is formed as a portable hand-held unit, here as a tablet-PC. On the jointly used display, product specific information is shown concerning the shoes listed in the hit list, which can be presented by the shoe sales person directly to the customer.

The invention claimed is:

1. A measuring method for determining biometric data of human feet, comprising the following steps:
    providing a reference object, which has at least one reference pattern;
    providing a freely moveable image recording device;
    automatically detecting a relative position and an alignment of the image recording device relative to the reference object using the at least one reference pattern;
    automatically recording several images by the image recording device wherein each individual image is only recorded, when the relative position and the alignment of the image recording device relative to the reference object corresponds to a triggering position predetermined for the respective image; and
    determining biometric data of the at least one foot by means of the recorded images.

2. The measuring method according to claim 1, further comprising:
    the step of determining the biometric data of the at least one foot by means of the recorded images comprises at least the following partial steps:
    generating at least one three-dimensional model of the at least one foot placed on the reference object by a processing device on the basis of the recorded images; and
    determining the biometric data of the at least one foot by the processing device using the at least one three-dimensional model.

3. The measuring method according to claim 1, further comprising:
    a pedestal for determining biometric data of human feet is provided comprising:
    a base plate, on which at least one to be measured human foot is placeable, wherein the base plate has a geometric base-sided reference pattern; and
    a wall element, which splits the base plate into two halves and which is arranged transversally to the base plate, for each half of the base plate a mirror arranged transversally to the base plate, wherein the wall element has on the sides facing the mirrors respectively a geometric wall-sided reference pattern and wherein respectively a reflective mirror face of the mirrors is arranged opposite to one of the wall-sided reference patterns is used, wherein the reference object comprises the pedestal.

4. The measuring method according to claim 1, further comprising:
    a pedestal for determining biometric data of human feet is provided comprising:
    a base plate, on which at least one to be measured human foot is placeable, wherein the base plate has a geometric base-sided reference pattern;
    a wall element, which splits the base plate into two halves and which is arranged transversally to the base plate, for each half of the base plate a mirror arranged transversally to the base plate, wherein the wall element has on the sides facing the mirrors respectively a geometric wall-sided reference pattern and wherein respectively a reflective mirror face of the mirrors is arranged opposite to one of the wall-sided reference patterns; and
    a freely movable image recording device for recording several images of the at least one placed foot is used, wherein the reference object comprises the pedestal.

5. The measuring method according to claim 1, further comprising the following step:

putting out instructions for transferring an image recording device to the respective triggering position.

6. The measuring method according to claim 5, further comprising
that before the putting out of the respective instruction for transferring the image recording device to the respective triggering point, the following steps are provided:
automatically detecting the relative position and the alignment of the image recording device relative to the reference object by using the at least one reference pattern; and
calculating a path from the detected relative position with the detected alignment to the respective triggering position.

7. The measuring method according to claim 5, further comprising
that the instructions for guiding the user is carried out via optical or acoustic indication elements.

8. The measuring method according to claim 1, further comprising
that, furthermore, the following steps are provided:
comparing the determined biometric data of the at least one foot with sets of data of shoes, which comprise at least information of the shoe sizes or of shoe shapes of various shoes, by an evaluation device;
transferring a hit list with shoes fitting the biometric data from the evaluation device to an out-put device; and
reproducing information relating to the shoes listed in the hit list.

9. A pedestal for determining biometric data of human feet comprising:
a base plate on which at least one to be measured human foot is placeable, wherein the base plate has a geometric base-sided reference pattern; and
a wall element which splits the base plate into two halves and which is arranged transversally to the base plate, for each half of the base plate a mirror arranged transversally to the base plate, wherein the wall element has on the sides facing the mirrors respectively a geometric wall-sided reference pattern and wherein respectively a reflective mirror face of the mirrors is arranged opposite to one of the wall-sided reference patterns.

10. A pedestal according to claim 9, wherein
the wall element and the base plate are arranged at an angle to each other, which is in the range between 70 and 140 degrees.

11. A pedestal according to claim 9, wherein
the base plate and/or the wall element has/have a retro-reflective surface.

12. A pedestal according to claim 9, wherein
the mirrors are arranged at an angle to the base plate, which is in the range between 70 and 160 degrees.

13. A pedestal according to claim 9, wherein
the pedestal is formed symmetrically to a plane formed by the wall element.

14. A measuring system for determining biometric data of human feet, comprising:
a pedestal, for determining biometric data of human feet, comprising a base plate, on which at least one to be measured human foot is placeable, wherein the base plate has a geometric base-sided reference pattern, a wall element, which splits the base plate into two halves and which is arranged transversally to the base plate, for each half of the base plate a mirror arranged transversally to the base plate, wherein the wall element has on the sides facing the mirrors respectively a geometric wall-sided reference pattern and wherein respectively a reflective mirror face of the mirrors is arranged opposite to one of the wall-sided reference patterns; and
a freely movable image recording device for recording several images of the at least one placed foot.

15. The measuring system according to claim 14, wherein
a processing device, which is formed such, that a three-dimensional model of the at least one foot can be generated from the images and that by means of the model biometric data of the at least one foot are determinable;
an evaluation device formed such, that the determined biometric data is comparable with sets of data of shoes using stored shoe sizes and/or shoe shapes and the shoes fitting to the determined biometric data are identifiable; and
an out-put device, formed such, that information concerning the fitting shoes are reproducible,
are provided.

16. The measuring system according to claim 15, wherein
the image recording device and the out-put device form a portable structural unit and that the processing device as well as the evaluation device are structurally separately formed from the image recording device and the out-put device.

* * * * *